US00PP10905P

United States Patent [19]

Hammond

[11] Patent Number: Plant 10,905

[45] Date of Patent: May 18, 1999

[54] *ARGYRANTHEMUM FRUTESCENS* CULTIVAR NAMED 'ANNABEL'

[76] Inventor: Frank Hammond, Narre Warren East, Victoria, 3804, Australia

[21] Appl. No.: 08/851,475

[22] Filed: May 5, 1997

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 10,298 3/1998 Cunneen ..... Plt./68.1

*Primary Examiner*—Howard J. Locker
*Assistant Examiner*—Kent L. Bell

[57] ABSTRACT

A new and distinct selection of Silver Flower which shall be referred hereinafter as *Argyranthemum frutescens* cultivar 'Annabel'. *Argyranthemum frutescens* cultivar 'Annabel' differs distinctively from other *Argyranthemum frutescens* plants by its unique combination of a large growth habit with yellow green foliage and large white blooms with distinct yellow centers that are produced profusely at a young age.

1 Drawing Sheet

BACKGROUND OF THE INVENTION

This invention relates to a new and distinct selection of *Argyranthemum frutesens* (L.) Schultz-Bip, native to the Canary Islands and a member of the Compositae family. *Argyranthemum frutescens* cv. 'Annabel' was a result of an uncontrolled breeding program. My selection was found among non clonal *Argyranthemum frutescens* plants and neither the seed nor pollen parent is known. I selected this seedling progeny in January 1993. My discovery was made at 100 Boundary Road, Narre Warren East, Victoria, Australia. Selection was based on the attributes of the large habit and large profuse flowers. My new plant has been asexually reproduced by cuttings since the discovery in 1993 at 100 Boundary Road, Narre Warren East, Victoria, Australia and later at Monrovia Nursery Company, 18331 E. Foothill Boulevard, Azusa, Calif. Had this chance seedling not been discovered and propagated, it may have been lost to mankind. It is unlikely these particular select and favorable attributes of this plant could be conveyed to progeny through sexual reproduction in the next generation. However, through extensive propagation by rooting of the plant it has been established that the novel exceptional characteristics of this plant are stable and reliably passed on the clonal specimens through asexual reproduction.

SUMMARY OF INVENTION

*Argyranthemum frutescens* cv. 'Annabel' was selected to replace an existing variety we grew named *Argyranthemum frutescens* cv. 'Single White'. Cultivar 'Single White' is a large grower achieving a height of 2 meters and 3 meters in width, with large 6–8 centimeter flowers. My selection cultivar 'Annabel' has a smaller more compact habit than the original cultivar 'Single White'. Cultivar 'Annabel' also produces more profuse and smaller flowers which begin to bloom earlier in the season and on a much younger plant than the cultivar 'Single White'. My selection cultivar 'Annabel' has tolerated a minus 5 degrees Celsius which is equivalent to U.S.D.A. hardiness zone seven with no harm or damage. Winter protection is necessary from heavy frost.This application is co-pending with those of four other Argyranthemum selection. Both Gretel (U.S. Plant Patent Application 08/846,475) and Carmella (U.S. Plant Patent Application 08/846,477) differ significantly in their pink ray florets. Primrose Petite (U.S. Plant Patent Application 08/848,790) posseses yellow ray florets. The final Selection 'Blanche' (U.S. Plant Patent Application 08/846,476) differs significantly in having a dense smaller overall growth habit of almost 30 c.m. Shorter and 8 cm less wide.

BRIEF DESCRIPTION OF ILLUSTRATION

The accompanying photograph shows the plant in flower. The large bloom consisting of white ray florets and yellow disc florets are prominently displayed.

BOTANICAL DESCRIPTION

Below is a detailed description of *Argyranthemum frutescens* cultivar 'Annabel', the color terminology is from The Royal Horticultural Colour Charts. Measurements are based on 20 random samples taken in Australia.

Overall habit: Perennial, large, subshrub.

Overall size: Largest size of 5 selections when compared to cultivars 'Gretel', 'Primrose Petite', 'Carmella', 'Blanche'. Height: 52 cm±2.5 cm in California. Width: 46.8 cm±5.2 cm.

Bloom season in Australia: Heaviest bloom in Spring for 10 weeks. Some flowers present throughout the year.

*Melbourne.*—8 to 10 months per year.

*Brisbane.*—6 to 8 months per year.

Bloom lastingness: 7 to 14 days per flower.

Folige:

*Arrangement.*—Alternate.

*Surface.*—Upper: glabrous, lightly canescent. Lower: glabrous.

*Shape.*—Deeply parted, pinnatisect, primary segments 5.

*Margins.*—Smooth, lobes end with a mucronulate tip.

*Size.*—Length: 77.3 mm (±9.8 mm); 68.0 mm–58 mm in California. Width: 36.8 mm (±2.6 mm); 30 mm–29 mm in California.

*Color.*—Upper leaf surface: Yellow-Green 146B (Spinach Green 0960-British Horticultural Color Chart). Lower leaf surface: Yellow-Green 146B (Spinach Green 0960/3-British Horticultural Color Chart).

*Texture.*—Slightly fleshy, thin succulent.

*Stem.*—Coloration Scheeles Green 860/1.

Inflorescence:

*Bud shape.*—Globose.

*Bud length.*—6 mm.

*Bud width.*—6 mm.

*Bud color.*—Scheeles Green 860/1 paper like bracts Spanish Orange 010/3.

*Arrangement.*—Heterogamus capitula, 1 per peduncle.

*Peduncle length.*—7.5 cm to 13 cm in length.

*Capitulum diameter.*—Size varies in Australia and California due to climate and fertilization. The higher the nitrogen level the larger the plant and flower. 47.3 mm (±1.76 mm) in Australia; 36.0 mm to 45.mm in California.

*Capitulum height.*—Base of involucre to top of capitulum 15.9 mm (±1.4 mm); 10–12 mm in California.

*Disc diameter.*—1.0 cm to 1.5 cm in California.

*Disc floret reproductive organs.*—Pistillate and staminate organs are present.

*Disc color.*—Yellow-Orange 14A and Yellow 13A (Chinese Yellow 606-British Hortiultural Color Chart).

*Ray floret number.*—Average 20–22.

*Ray floret reproductive organs.*—Pistillate organs present.

*Ray floret aspect.*—Flattened at right angles to peduncle at full anthesis.

*Ray floret shape.*—Ligulate.

*Ray floret length.*—18 mm+/−3 mm.

*Ray floret width.*—6 mm+/−2 mm.

*Ray floret color.*—White 155D-no fading with age (No equivalent white shade in British Horticultural Color Chart) on upper surface and lower surface.

*Basal line.*—Not present.

*Fragrance.*—Slight faint scent to inflorescence.

Fruit: A 2–4 angled cypsela, 1 winged.

Disease resistance: Rust diseases of the genera Coleosporium sp. and Cronartium sp. are not known to occur on this plant in Australia.

I claim:

1. A new and distinct *Argyranthemum frutescens* plant substantially as shown and described which differs distinctively from other *Argyranthemum frutescens* plants by its unique combination of a large growth habit with yellow green foliage and large white blooms with distinct yellow centers that are produced profusely at a young age.

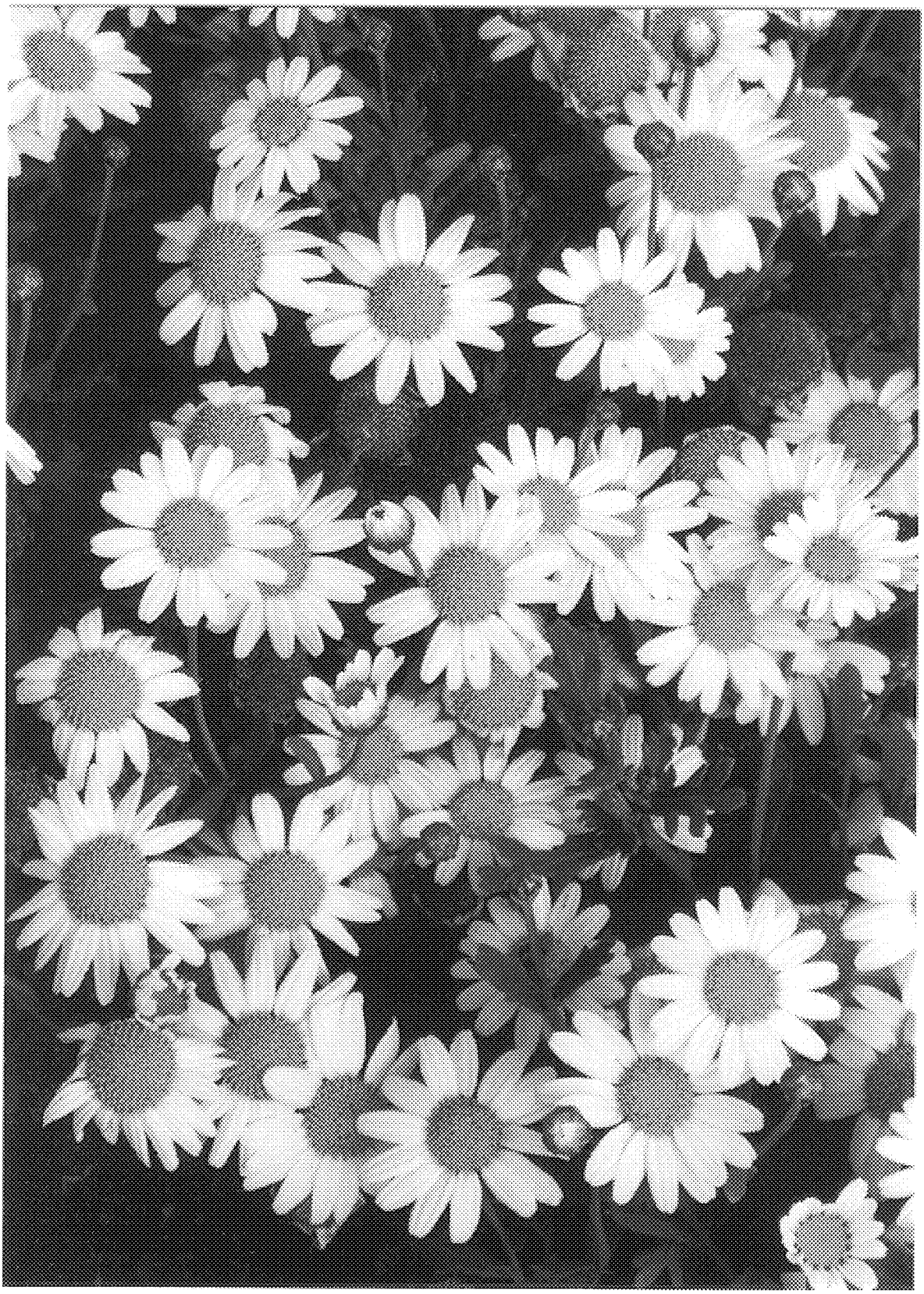

* * * * *